United States Patent [19]
Berthon

[11] 3,931,526
[45] Jan. 6, 1976

[54] PROCESS AND A DEVICE FOR MEASURING TRANSMISSION FACTORS

[75] Inventor: Aime Marie Berthon, Paris, France

[73] Assignee: Aerazur Constructions Aeronautiques, Issy-les-Moulineaux, France

[22] Filed: Apr. 9, 1974

[21] Appl. No.: 459,435

[30] Foreign Application Priority Data
Apr. 13, 1973 France .............................. 73.13574
Mar. 12, 1974 France .............................. 74.08381

[52] U.S. Cl. .............................. 250/575; 356/206
[51] Int. Cl.² .............................. G01H 21/26
[58] Field of Search ........... 250/564, 565, 573, 575; 356/204, 205, 206, 207

[56] References Cited
UNITED STATES PATENTS

| | | | |
|---|---|---|---|
| 2,427,013 | 9/1947 | MacAdams | 356/206 |
| 3,091,690 | 5/1963 | McHenry | 250/575 |
| 3,233,781 | 2/1966 | Grubbs | 250/565 |
| 3,447,370 | 6/1969 | Tanzman | 250/565 |
| 3,629,589 | 12/1971 | Gleixner | 356/204 |
| 3,698,820 | 10/1972 | Hanff et al. | 250/573 |
| 3,720,813 | 3/1973 | Badessa | 250/565 |
| 3,745,350 | 7/1973 | Hill et al. | 356/207 |
| 3,746,452 | 7/1973 | Remy et al. | 356/206 |
| 3,788,745 | 1/1974 | Menke | 356/204 |

*Primary Examiner*—James W. Lawrence
*Assistant Examiner*—D. C. Nelms
*Attorney, Agent, or Firm*—Sughrue, Rothwell Mion Zinn & Macpeak

[57] ABSTRACT

A device for measuring transmission factors is comprised of an emitter of light impulses located at a distance from a main photoreceiver. The emitter and the main photoreceiver are optically conjugated by mirrors. An auxiliary photoreceiver located adjacent to the light emitter receives a constant portion of the flux emitted by this emitter and a flux coming from the ambient light. By establishing the ratio between the impulse-type electric signals transmitted by these photoreceivers, a value proportional to the transmission factor measured between the emitter and the main photoreceiver is obtained.

8 Claims, 4 Drawing Figures

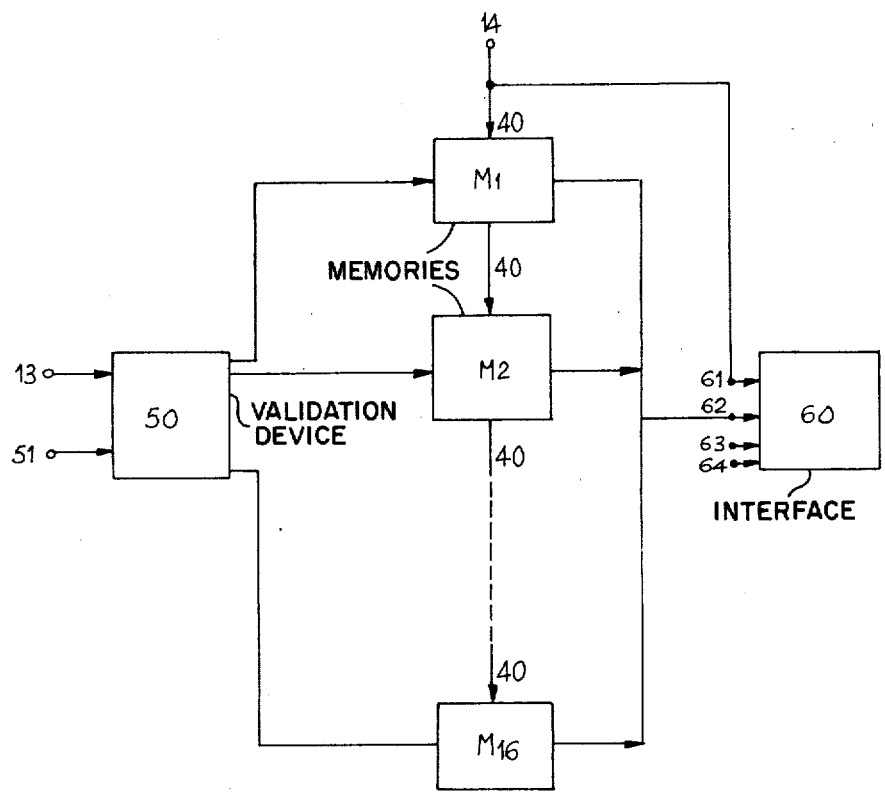

PROCESS AND A DEVICE FOR MEASURING TRANSMISSION FACTORS

BACKGROUND OF THE INVENTION

1. Field of the Invention

The present invention relates to a process for measuring transmission factors and more particularly to a process for measuring atmospheric transmission factors and a device employing this process.

2. Description of the Prior Art

As is disclosed in the monograph No. 76 of the French National Meteorological Service published in August 1970, the transmission factor T is defined for a light beam as the ratio of the light fluxes at the beginning and end of an optical path of specified length in a dim atmosphere. This factor is sometimes known as the transmittance $\tau$ for a defined path of predetermined length. Devices for measuring the transmission factor of the atmosphere are generally known as transmissometers. The basic principle of a transmissometer consists in measuring the average transmissivity of the atmosphere along a predetermined path. In practice this involves arranging a projector with a constant flux having perfectly defined optical and mechanical features so that it illuminates a receiver which also has a well defined geometry and which is situated at a distance D from the projector. The current or output voltage of the receiver enables the transmittance of the density of the interposed atmosphere and thus its average transmissivity to be determined, the transmissivity being the transmission factor per unit of length.

A device of this type can also be graduated directly in terms of meteorological visibility by using formulae linking these quantities to transmission factors. The visibility is the maximum distance at which a reference can be identified by an average observer.

A distinction is drawn between the daytime meteorological visibility and nighttime meteorological visibility. The daytime meteorological visibility or visibility by contrast is defined as the greatest distance at which a dark object of suitable dimensions situated close to the earth can be seen and identified when it is observed against a background of mist or sky on a generally horizontal plane. The nighttime meteorological visibility which is a physical feature of the atmosphere is determined from observation of specific light sources as being the distance at which the coefficient of extinction reaches a certain value. According to the Koschmieder theory the relationship between the transmission factor T and the visibility by contrast V for a path having the length D is the following:

$$T = e^{-\frac{L}{V} \ln \frac{1}{\epsilon}} \quad (1)$$

where $\epsilon$ is the coefficient of extinction for which the value $$0.025 \left( \ln \frac{1}{\epsilon} = 3.7 \right)$$

is generally selected for meteorological purposes and the value $$0.05 \left( \ln \frac{1}{\epsilon} = 3 \right)$$

for aeronautical purposes. According to the Allard theory the relationship between the transmission factor and the nighttime visibility V' (or the visibility of a light source) is the following:

$$T = e^{\frac{L}{V'} \ln \frac{I}{E_t V'^2}} \quad (2)$$

where $I$ is the intensity of the light source and $E_t$ a threshold of visual illumination, this value $E_t$ being based on the ambient light according to the defined norms. This visibility measurement is especially useful for airports, highways or motorways.

If the principle of measuring transmittance indicated above were applied directly to a transmissometer, gross errors would result. In the first place, the flux emitted is not known precisely. It is a function of the dispersion of the active emission elements and the time and temperature. Secondly, the flux received is a function of the gain of the photoreceiving cell, and it also depends on the features of these cells and on their variation with time and temperature. In addition, the flux received has also been contributed to by the ambient light which tends to falsify any measurement.

Various types of transmissometers have been proposed in the prior art to obviate these disadvantages. Firstly there are transmissometers in which a calibration of the emitting lamp is first obtained by using a reference path between this lamp and the photoreceiving cell and by effecting the switching operation between these two paths by mechanical means. There is no need to enumerate at this point the disadvantages of these mechanical devices which result essentially from the permanent maintenance which they require. Static devices were then developed. All these devices are based on the idea that it is necessary to free the emitters and receivers from variations and the light fluxes emitted are modulated to separate them from the ambient light fluxes. For example, it is possible to cite a device comprising a double emitter- receiver unit designed to correct errors due to the aberrations of these various elements. One obvious disadvantage of a device of this kind is the complexity of its elements. There are other devices where there is an optical coupling between the emitter and the remote receiver. This optical coupling involving constant losses is constituted, for example, by means of optical fibers. One disadvantage of this type of device consists in the very need for an optical coupling which requires very long optical fibers when there is a fair distance between the receiver and the emitter. Very long optical fibers of this type are in fact expensive and their length is by necessity dictated by the limits of current technology.

SUMMARY OF THE INVENTION

The primary object of the present invention is thus to provide a process for measuring static transmission factors which does not involve any of the above disadvantages.

Another object of the present invention is to provide a transmissometer in which the coupling between the main emitter and the main receiver is effected by electronic means and not optical means.

Another object of the present invention is to provide a transmissometer which is also capable of providing a measurement of the ambient light.

A further object of the present invention is to provide a sufficiently simple and compact computing means which can be integrated in the sensing element of the transmissometer itself, thereby permitting determination in situ of the visibility.

To obtain these objects and others, the measuring process according to the present invention consists in using a main light emitter and a main photoreceiver situated at a desired distance D from one another. As is known, this distance is a function of the range of visibility distances which it is wished to measure. An auxiliary photoreceiver is provided adjacent to the main emitter and it provides an electric signal which is proportional to the light flux emitted by the main emitter. The optical path between the emitter and this auxiliary photoreceiver is either loss-free or subject to constant losses. The auxiliary photoreceiving cell and the main photoreceiving cell are such that they possess dynamic gains, the ratio of which is constant in respect of the illumination, temperature and time, that is, their dynamic gain characteristics are linear and stable. Consequently, if an electronic process is selected so that the main and auxiliary photoreceivers separate the electric signals R and r, respectively, coming from the light flux $\phi_E$ emitted by the main emitter, from the parasitic light fluxes coming, for example, from the ambient light, the ratio R/r equal to $K\phi_R/K'\phi_r$, is proportional, according to a known proportionality factor, to the ratio defining the transmittance: $\phi_R/\phi_E$ since $\phi_r$ is proportional to $\phi_E$, K and K' being the dynamic gains of the main photoreceiver and the auxiliary photoreceiver respectively. $\phi_R$ and $\phi_r$ are the fluxes received by the main and auxiliary photo receivers respectively and associated with the flux $\phi_E$ emitted by the main emitter. If, as has been previously stated, the auxiliary and main receivers have dynamic gains of constant ratio, the ratio K/K' is constant and a quantity is obtained with great precision proportional to the ratio of the flux received by the main receiver to the flux emitted by the main emitter. This quantity does not depend on the variation in the power of emission but solely on the reliability of the main and auxiliary receivers with respect to their dynamic gain characteristics. The auxiliary photoreceiving cell also enables ambient light to be received independent of any optical means and over a fairly wide aperture angle.

According to the present invention it is also proposed to provide a plurality of memories, possibly in the electronic circuit of the transmissometer, each of these memories containing different visibility values, with different addresses corresponding to different values of the transmission factor. Each of these memories is validated by the validation circuits as a function of the other parameters involved which are cited above, such as the ambient light and the intensity of a landing lights. Thus it is possible to consider each memory as comprising a visibility curve as a function of the transmission factor for a given value of different parameters.

The circuit incorporated in the sensor may also comprise interface means for transmitting by way of a telephone line, for example, output data from the memories to a control station. This interface means comprises parallel-to-series word conversion means.

These and other objects features and advantages of the present invention will be made apparent from the following detailed description of the preferred embodiment thereof provided with reference to the accompanying drawings.

BRIEF DESCRIPTION OF THE DRAWINGS

FIG. 4 shows a diagram of the electronic circuit to be connected to the circuit of FIG. 3 to provide visibility data.

DESCRIPTION OF THE PREFERRED EMBODIMENTS

Figure 1:
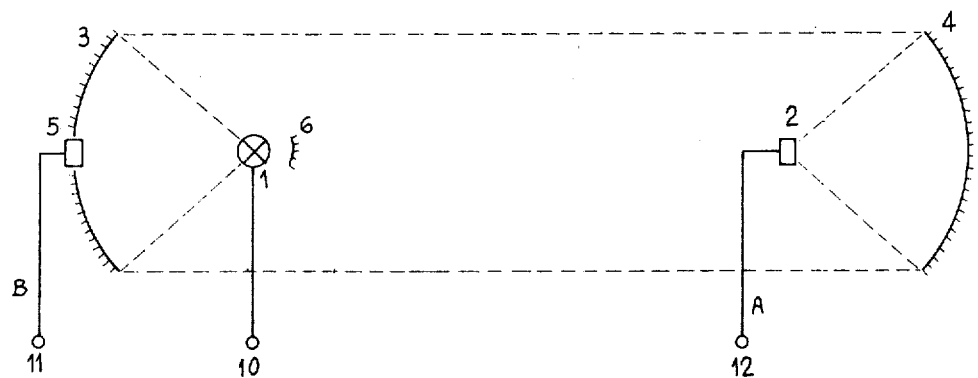
FIG. 1 is a diagrammatic view representing essentially the optical part of a transmissometer according to the present invention.

FIG. 1 shows an embodiment of the present invention. A main light emitter 1 emits a light beam in the direction of the main photoreceiver 2 by way of optical conjugation means. In this embodiment, the conjugation means consist of spherical or parabolic mirrors 3 and 4, at the focal points of which are located the main emitter and the main photoreceiving cell respectively. A mirror 6 may possibly be used depending on the source employed. An auxiliary photoreceiving cell is located at the center of the mirror 3 which is transparent at this point. This cell which is located immediately adjacent to the main emitter produces an electric signal B on a terminal 11. This signal B is the superposition of an electric signal r resulting from the light flux coming from the main emitter and of a second electric signal produced by the ambient light. The main receiver 2 also produces an electric signal A on the terminal 12. This signal is the super-position of a first signal associated with the flux emitted by the main emitter and disturbed by the optical medium crossed and of a second signal produced by ambient disturbances. To separate these two types of signals received respectively by the main receiver and the auxiliary receiver, a feed signal is supplied to a terminal 10 of the main emitter in such a way that the emission is effected in the form of impulses. In a preferred embodiment of the invention this main emitter is a photodiode emitting in the domain of the near infrared. Detailed studies have shown that in the majority of concrete cases visibility measured in the infrared is the same as visibility measured in the visible.

Figure 2:
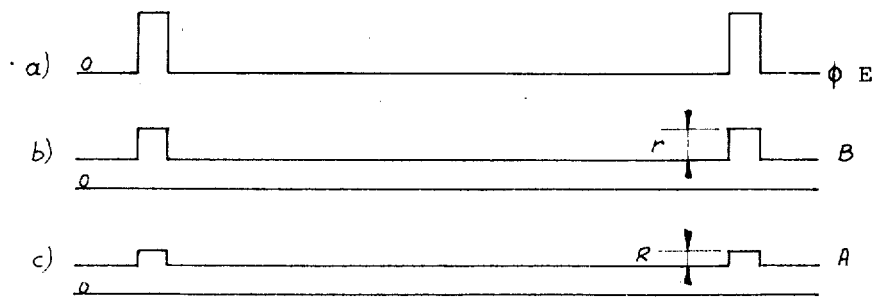
FIG. 2 shows the electrical wave forms emitted by the main light emitter and received by the main and auxiliary photoreceivers.

In FIG. 2, the curve a represents the flux emitted by the source 1. This flux is emitted during gaps of short duration in relation to the repetition rate. Curve b represents the electric signal B emitted by the auxiliary photoreceiver 5. This signal is the superposition of a continuous signal and of impulses of height r proportional to the flux $\phi_r$ received by the cell 5 from the emitter 1, that is, proportional to $\phi_E$. Curve c represents the signal A emitted by the photoreceiving cell 2. This signal is the superposition of a continuous base and an impulse signal of height R. The signal R is produced by the flux emitted by the source 1 and reflects disturbances arising in the optical medium traversed.

A preferred embodiment of an electronic circuit intended to provide the relationship between R and r will now be described in reference to FIG. 3. This circuit comprises two input terminals 11 and 12 which are the output terminals of the auxiliary and main photoreceivers respectively. A filter 31 is connected to the terminal 11 and a signal which is proportional to the ambient light is obtained at the output 13 of this filter 31. No optical system is placed in front of the auxiliary photoreceiving cell and its aperture angle is broad. In addition, the contribution of the signal r is very slight in view of the low form factor of this signal. This output signal proportional to the ambient light is accessible on a terminal 13. The signal obtained at this terminal 13 may be used directly or transmitted to a computing element to determine the visual threshold of illumination $E_t$ introduced in formula (2). Thus a transmissometer according to the present invention associated with a suitable computing element enables the meteorological daytime or nighttime visibility as defined above to be calculated.

A circuit known as the ground clamping circuit 32 which is of a type known per se is also connected to the input terminal 11. Impulses r referenced on the ground are obtained at the output of this ground clamping circuit. These impulses r are transmitted to a hybrid multiplier 33 which is also connected to a counter 34 with N stages. The output of the hybrid multiplier 33 is connected to a first input terminal of a comparator 35. The other input terminal of this comparator 35 is connected to the output of a second ground clamping circuit 36, the input of which is connected to the terminal 12. This ground clamping circuit produces the signal R referenced to ground. Amplifiers or reducers which are not shown may also be inserted in one or other of these input chains. When the product of r by a number n obtained at the output of the hybrid multiplier 33 is equal to R, the comparator 35 transmits a transfer order to a shift register 37 connected to the counter 34. As the gains in the input and output chains are known, this number n is proportional to the transmittance, for example, it can provide directly the value of the transmissivity in per cent, in terms of a thousand, or in any other desired unit. The precision of the measurement is associated with the number N of stages in the shift register, that is, also with the capacity of the counter and of the hybrid multiplier.

An output 14 of the shift register provides the value of the transmission factor directly in digital form. The output of the shift register may also be transmitted to a digital/analog converter 38 and then to a filter 39 designed to obtain an average in time of the transmittance value. A terminal 15 at the output of this filter 39 may be connected to any analog measuring or recording device. The possibility of obtaining a digital value associated with the transmittance on the terminal 14 itself enables calculations providing the visibility values corresponding to the transmittance measured to be effected by means of a small computer without any intermediate measures. A time measurement circuit which is not shown is connected to the terminal 10 of the source 1, to the ground clamping circuits 32 and 36, to the counter 34 and to the shift register 37 to ensure that these different devices operate in synchronism. The electronic circuit as represented in FIG. 3 provides a precision which in all cases may be greater than the precision resulting from the parts of the measurement chain. In a preferred embodiment $N = 2^8 = 256$. Thus the relative precision is then $4 \cdot 10^{-3}$.

According to the present invention, to increase the precision of the measurement, the temperature of the unit comprising the emitter 1 and the auxiliary receiver 5 is roughly stabilized and the main receiver 2 is governed by the unit to ensure that it is permanently at the same temperature as the first unit. This precaution is generally not necessary. In fact, the emitter and the main receiver are generally located at distances in the order of some tens of meters and as a result their temperatures are approximately identical. Furthermore, it is an illusion to want to increase the precision of the measurement at all costs owing to the fact that this measurement is basically known to comprise an error owing to the irregularity of mists or other disturbances — the effects of which on the transmission factor of a light beam it is wished to measure.

In addition, a number of safety devices are provided for permanently ensuring that the transmissometer according to the present invention operates correctly and to authenticate the measurements taken. Firstly, the highest value of the impulse r provided by the auxiliary photoreceiver is recorded in the memory and compared to a threshold value and if the emission power decreases more than 20% an alarm is triggered. This alarm is also triggered if the feed voltage ceases to flow. Secondly, in the case of dense fog it is possible to perceive a practically zero level at the main receiver. To check that this receiver is operating correctly, an emitting light source having a controlling function is disposed adjacent to the main photoreceiver which thus constantly receives a minimum light level which corresponds to a minimum electric signal emitted by this main photoreceiver. Consequently, the electric output signal from the main photoreceiver is constantly compared to a threshold value and an alarm is triggered if it falls below this threshold value. This alarm is also raised if the feed voltage of the main photoreceiver ceases to flow. Other alarm signals are provided to ensure the correct operation of the series processing. More particularly, as the unit is operated on a general time basis, any hold-up in this time schedule produces an alarm signal at the main emitter. To check the series processing part, an alarm is triggered if the counter 34 does not attain the state 1 with each measuring cycle. An alarm signal is also triggered if the feed voltage which is constantly compared to a threshold value set by a Zener diode falls more than 20%. All these alarm elements are assembled on a filtered hysteresis relay having a regulatable time constant. Thus the device comprises a general alarm signal which is free of interference in the event of any fluctuation of the parameters about the limit values. This signal may be telecommunicated by wire or radio.

The present invention may be used in particular for obtaining visibility measurements at airports, on roads and motorways, in ports and channels. It can also be used to study pollution, for example, in underground passages or in pipelines. It should be noted that the extreme precision, which is provided by a transmissometer according to the present invention and which is voluntarily limited when this is used solely for measuring visibility may be rendered more precise when it is used for other applications (this precision may be greater than 0.5%).

Figure 3:
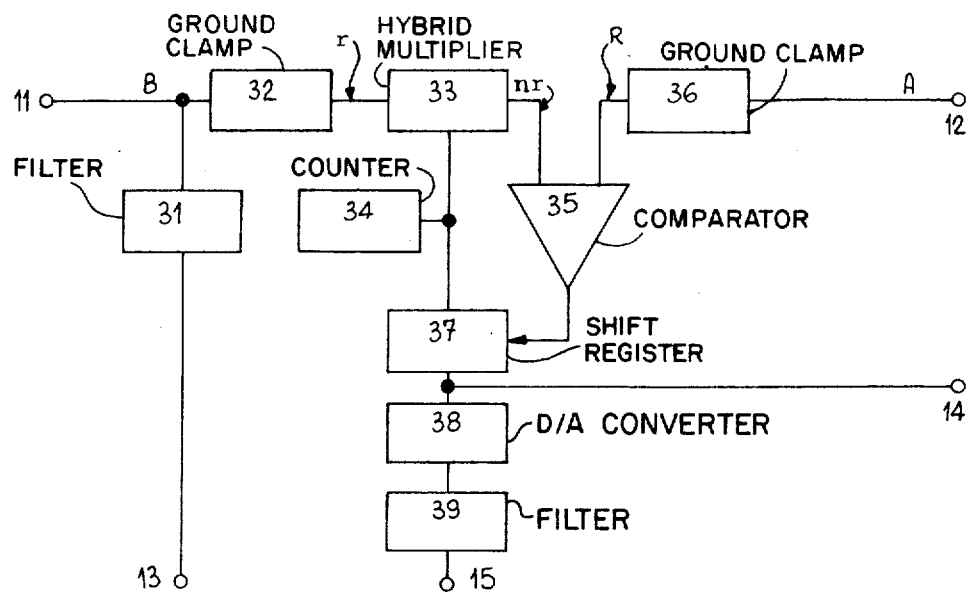
FIG. 3 shows a diagram of the electronic circuit adapted for the present transmissometer.

With reference to FIG. 4, the reference numerals 13 and 14 represent the input terminals of the ambient light signal in analog form and of the signal of the transmission factor in digital form respectively (these terminals 13 and 14 are the same as those shown in FIG. 3). The terminal 14 is connected by way of a line (bus) 40 to the address inputs of the memories $M_1 - M_{16}$. These memories are generally MOS memories.

In the embodiment described, there are sixteen memories $M_1 - M_{16}$. In fact, one of the important aspects of the present invention consists in the discovery by the Applicant of the fact that it is senseless to try to obtain a high degree of precision in the final visibility values and that at all events it is senseless to attempt to obtain precisions in excess of 10% owing to the variations in the physiological parameters involved in determining visibility. The Applicant has discovered that by quantizing the different values of the ambient light at four levels and by quantizing the levels of light source illumination, like wise at four levels, it is possible to obtain adequate precision. Thus, from an ambient light signal reaching the terminal 13 from the transmissometer described hereinabove and from a representative signal of the light source illumination reaching the terminal 51, it is possible to quantize these two signals respectively with the validation device 50 at four levels and thus to validate one of the memories $M_1 - M_{16}$.

By way of example, it is possible to cite a suitable quantization for the levels of ambient light as consisting in choosing four ranges: $L_1, L_2, L_3, L_4$, such that:
$L_1 < 50$ cd/m²
$50 < L_2 < 1000$ cd/m²
$1000 < L_3 < 12.000$ cd/m²
$L_4 > 12.000$ cd/m²

Thus one of the memories $M_1 - M_{16}$ is validated. This memory receives as an address signal the value of the transmission factor. Owing to the values prerecorded in this address the memory provides at its output the visibility value corresponding to the value of the transmission factor, of the ambient light and of the light source (such as landing lights) illumination.

The digital visibility output is transmitted to a terminal 62 of an interface 60 which also receives value signals of the transmission factor 14 at a terminal 61 and other selected signals at the terminals 63,64 . . . This interface 60 puts all the data into digital form and effects a parallel-to series word conversion to permit transmission to a central station. It is also possible to provide indication means on the transmissometer itself.

In a preferred embodiment a central indicator unit interrogates the interface 60 and provides it with the value of the illumination of the strip, and this interface 60 responds by sending 8 words, each comprising 8 bits. Each word comprises 4 address bits and 4 information bits. By way way of example, the following are possible address signals:

| Address 0000 | : illumination of a runway |
| Address 0001 | : background illumination |
| Address 0010 | : alarms and written order of visibility |
| Address 0011 | : first half word of visibility |
| Address 0100 | : second half word of visibility |
| Address 0101 | : first half word of the transmission |
| Address 0110 | : second half word of the transmission factor. |
| Address 0111 | : free half word |

To restrict the consumption of the memories (which is in the order of 40 milliamps for each according to current technology) feed out only takes place during the time needed to transmit the visibility data.

The present invention is not limited to the embodiments which have been described but it can also be modified in manner apparent to the person skilled in the art without departing from the scope of the invention.

What is claimed is:

1. A device for measuring the atmospheric transmission factor between two points defining a fixed measurement path of predetermined distance and for determining the intensity of the ambient light, comprising:
   an emitter of light impulses located at one end of said measurement path,
   a main photoreceiving cell located at the other end of said measurement path for receiving light from said emitter through said measurement path and producing a first electrical signal,
   an auxiliary photoreceiving cell for receiving light from said emitter and ambient light and producing a second electrical signal, said main and auxiliary photoreceiving cells having linear and stable dynamic gain characteristics,
   a first mirror having a first focus,
   a second mirror having a second focus, said emitter being located at the focus of said first mirror and directing a substantially parallel light beam towards said second mirror, said main photoreceiving cell being located at the focus of said mirror, said auxiliary photoreceiving cell being located substantially at the apex of said first mirror whereby said auxiliary photoreceiving cell receives ambient light through a large aperture,
   filtering neams connected to said auxiliary photoreceiving cell for passing a d.c. signal component in said second electrical signal which is representative of the ambient light and,
   means connected to said main and auxiliary photoreceiving cells for dividing a pulsed signal component in said first electrical signal by a pulsed signal component in said second electrical signal to produce an output signal which is representative of said transmission factor.

2. A device according to claim 1, wherein said emitter of light impulses is an electro-luminescent diode emitting in the near infrared and said main and auxiliary photoreceiving cells are receiving diodes sensitive to the wave length emitted by said emitter.

3. A device according to claim 1, wherein said means for dividing comprises:
   a first ground clamping circuit connected to the output of said auxiliary photoreceiving cell for passing a pulsed signal component referenced to ground,
   a hybrid multiplier connected to receive as one input the output of said first ground clamping circuit and as the other input a signal representing a binary number, said hybrid multiplier generating an output signal proportional to the product of the pulsed signal component from said first ground clamping circuit and said binary number,
   a counter connected to receive the pulsed signal component from said first ground clamping circuit for accumulating a count,
   a second ground clamping circuit connected to the output of said main photoreceiving cell for passing a pulsed signal component reference to ground,
   a comparator having first and second input terminals, the outputs of said hybrid multiplier and said second ground clamping circuit being connected to said first and second input terminals, respectively, of said comparator,
   a shift register connected to receive the count accumulated by said counter in response to an output signal of said comparator which provides a transfer order to said shift register, the output of said shift register being connected to said other input of said hybrid multiplier as a result of which at the output of said shift register a digital value is obtained directly, this value representing the transmission factor between said emitter and said main photoreceiving cell.

4. A device according to claim 3, wherein said filtering means is an average value filter connected to the output of the auxiliary photoreceiving cell and providing a signal proportional to the ambient light.

5. A device according to claim 4, further comprising computing means for determining the digital value of the visibility as a function at least of the digital value of the transmission factor and the signal proportional to the ambient light.

6. A device according to claim 5, wherein said computing means comprises a plurality of memories, and a validation circuit, one of said memories being selectively validated at a given instant by a signal coming from said validation circuit receiving said ambient light signal, the digital signal of the transmission factor being transmitted to the address input of the memory validated which contains the value of the corresponding visibility.

7. A device according to claim 6, further comprising interface means for providing at least the values of the transmission factor of the ambient light and of the visibility.

8. A device according to claim 5, wherein said computing means receives as another parameter an electric signal corresponding to the lighting power of light sources such as landing lights on a runway.

* * * * *